US012693198B2

(12) United States Patent (10) Patent No.: US 12,693,198 B2
Alomair et al. (45) Date of Patent: Jul. 28, 2026

(54) PVT CELL EMBEDDED WITH POROUS MEDIA FOR RESERVOIR FLUID ANALYSIS

(71) Applicant: KUWAIT UNIVERSITY, Safat (KW)

(72) Inventors: Osamah Alomair, Safat (KW); Nyeso Christian Azubuike, Safat (KW); Mahmoud Mohamed Hassan Ali, Safat (KW); Ahmad Essam Abdel Halim Omar, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 19/035,562

(22) Filed: Jan. 23, 2025

(65) Prior Publication Data

US 2026/0210826 A1 Jul. 23, 2026

(51) Int. Cl.
*G01N 11/04* (2006.01)
*G01N 25/02* (2006.01)
*G01N 33/22* (2006.01)
*G01N 33/24* (2006.01)
*G01N 33/28* (2006.01)
(52) U.S. Cl.
CPC .............. *G01N 11/04* (2013.01); *G01N 25/02* (2013.01); *G01N 33/22* (2013.01); *G01N 33/241* (2013.01); *G01N 33/2829* (2013.01)
(58) Field of Classification Search
CPC ........ G01N 11/04; G01N 25/02; G01N 33/22; G01N 33/241; G01N 33/2829
See application file for complete search history.

(56) References Cited

U.S. PATENT DOCUMENTS

| | | | |
|---|---|---|---|
| 4,530,234 A | | 7/1985 | Cullick et al. |
| 5,665,594 A | * | 9/1997 | Schwarz ................ C12M 23/06 |
| | | | 435/298.2 |
| 5,747,674 A | | 5/1998 | Moracchini et al. |
| 6,289,725 B1 | * | 9/2001 | Hubbell .................. G01N 15/08 |
| | | | 141/47 |
| 7,628,058 B2 | | 12/2009 | Legrand |
| 8,230,747 B2 | | 7/2012 | Lindeberg |
| 8,797,517 B2 | | 8/2014 | Karnes et al. |
| 10,663,412 B2 | | 5/2020 | Nguyen et al. |

(Continued)

FOREIGN PATENT DOCUMENTS

| | | |
|---|---|---|
| CN | 105445270 A | 3/2016 |
| CN | 111693676 B | 12/2022 |

(Continued)

OTHER PUBLICATIONS

JP-2017536555-A (Year: 2017).*

*Primary Examiner* — Fatemeh Esfandiari Nia
(74) *Attorney, Agent, or Firm* — Nath, Goldberg & Meyer; Joshua B. Goldberg

(57) ABSTRACT

A system includes a chamber having a first portion, a second portion, a third portion, a fourth portion, and a fifth portion, with the second portion, the third portion, and the fourth portion located sequentially between the first portion and the fifth portion. An upper cell section located within the third portion. A lower cell section located within the fifth portion. A motorized piston located within the fifth portion. An inlet port in communication with the upper cell section. A heating oven enclosing the chamber. A visualization window in communication with the first portion and the second portion.

17 Claims, 1 Drawing Sheet

(56) References Cited

U.S. PATENT DOCUMENTS

| 2008/0016944 A1* | 1/2008 | Legrand | ............ | G01N 33/2823 |
| | | | | 73/25.01 |
| 2015/0117488 A1 | 4/2015 | Borges | | |
| 2018/0335374 A1* | 11/2018 | Kanj | .................... | G01N 33/241 |
| 2021/0055279 A1* | 2/2021 | Pujol | .................... | G01N 33/241 |
| 2023/0045547 A1* | 2/2023 | Nicot | .................. | G01N 33/241 |

FOREIGN PATENT DOCUMENTS

| FR | 3001546 A1 | 8/2014 | | |
| JP | 2017536555 A | * 12/2017 | ......... | G01N 33/2823 |

* cited by examiner

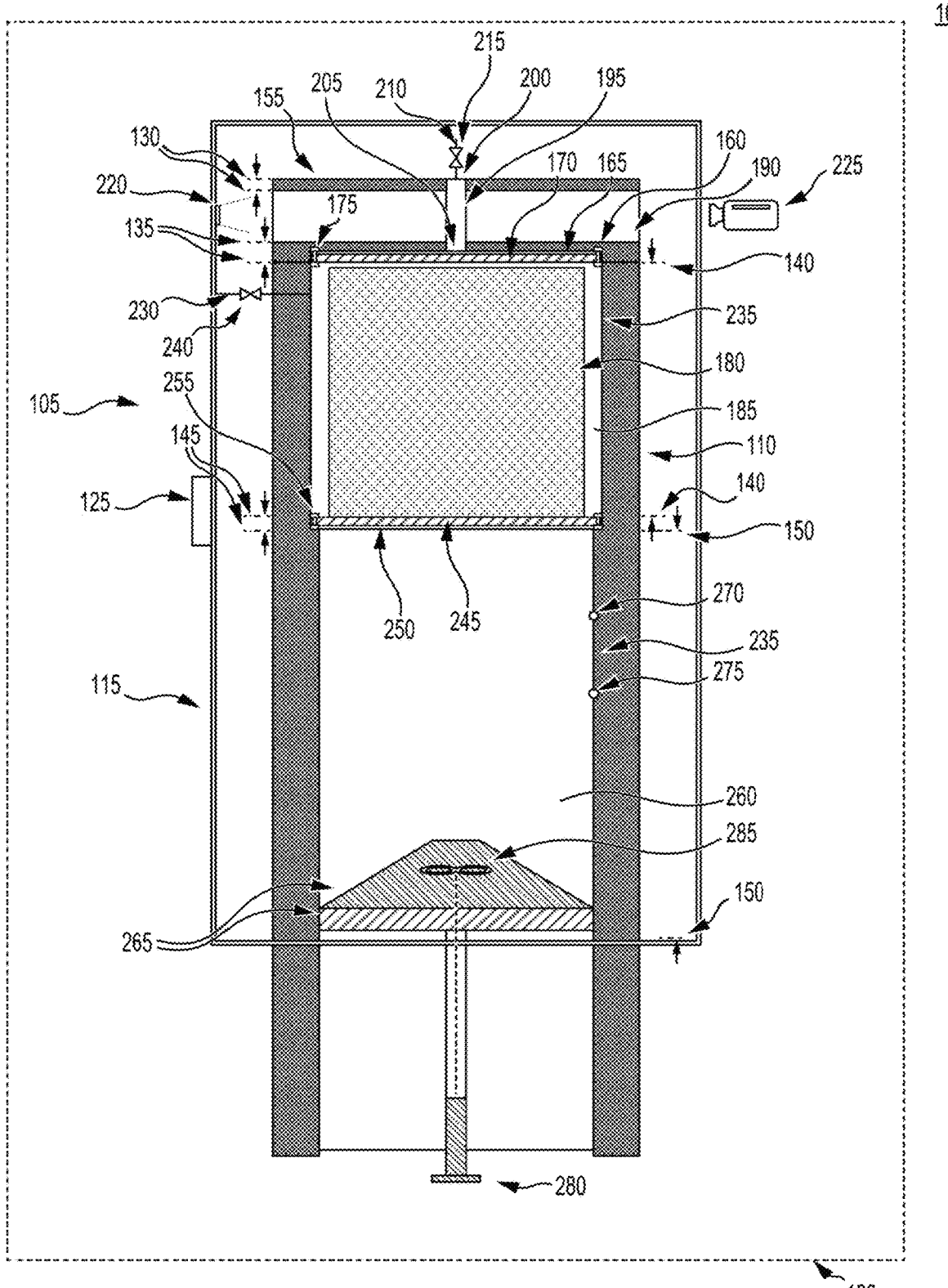

PVT CELL EMBEDDED WITH POROUS MEDIA FOR RESERVOIR FLUID ANALYSIS

FIELD AND BACKGROUND

The disclosure of the present application relates to a system, and particularly to a system and a method of using the system for analyzing at least one property of a fluid.

DESCRIPTION OF RELATED ART

A pressure-volume-temperature (PVT) cell is specifically designed to replicate conditions of a petroleum reservoir. Within the PVT cell, petroleum reservoir fluids are subjected to varying pressures and temperatures that mimic those in a petroleum reservoir, both before and during production. Such conditions are crucial for accurate analysis, as they significantly influence the behavior of the petroleum reservoir fluids. The conditions can inform decisions on how best to produce the petroleum reservoir fluids, including the design of surface facilities, selection of production methods, and prediction of future production performance. Typically, petroleum reservoir fluids can consist of both liquid and gas components. Changes in fluid density (compressibility) in the liquid and the tendency of gas to separate from the oil and gas solution during depressurization are of particular importance. Some examples of tests that can be performed on petroleum reservoir fluids include Constant Mass Expansion (CME), Differential Vaporization (DV), Flash Separation (FS), Constant Mass Depletion (CMD), and Constant Volume Depletion (CVD). These tests are well-established conventional petroleum fluid PVT tests typically conducted in a standard PVT cell.

In the early stages of PVT cell development, the behavior of hydrocarbon mixtures is typically analyzed using steel laboratory cells. The adjustment of fluid volume within the PVT cell, as well as the control of PVT cell pressure, can be achieved by pumping inert fluids, such as mercury, in and out of the PVT cell to the crude oil located within the PVT cell. However, handling mercury, particularly at elevated pressures and temperatures, poses several health risks. Consequently, other techniques for pressure control and volume variation are needed.

Typically, fluid studies in PVT cells are conducted using either constant or variable mass expansion in the PVT cell, without accounting for the effect of reservoir rock properties on the reservoir fluid phase behavior. This approach is flawed and does not accurately represent the actual fluid behavior in the reservoir. Physicochemical properties of petroleum reservoir fluids, such as those measured in PVT studies, are fundamentally influenced by the properties of the reservoir rock. For instance, while saturation pressure, which is often determined in a CME test, is primarily a function of fluid properties (i.e., composition, temperature, and pressure), certain rock properties such as porosity, permeability, fracture networks, wettability, capillary pressure, compressibility, pore size distribution, and tortuosity can impact how fluids behave within the reservoir. These rock properties can indirectly affect the conditions at which saturation occurs.

In light of the above, a need remains for a system and a method of using the system for analyzing at least one property of a fluid, such as a petroleum reservoir fluid, as the fluid is being absorbed by a porous media.

SUMMARY

The present subject matter relates to a system which, in one embodiment, includes a chamber. The chamber can include a first portion, a second portion, a third portion, a fourth portion, and a fifth portion, with the second portion, the third portion, and the fourth portion located sequentially between the first portion and the fifth portion. An upper cell section is located within the third portion and can be configured to receive a porous media and at least one fluid injected therein. A lower cell section is located within the fifth portion and can be configured to receive the at least one fluid flowing from the upper cell section through the fourth portion into the fifth portion. A motorized piston is located within the fifth portion and can be configured to pressurize the at least one fluid in the lower cell section. An inlet port can be in communication with the upper cell section and can be configured to inject the at least one fluid into the upper cell section. A heating oven can enclose the chamber and can be configured to heat the porous media and the at least one fluid in the upper cell section, the fourth portion, and the lower cell section. A visualization window in communication with the first portion and the second portion and can be configured to allow gas bubble formation and/or fog formation generated from the at least one fluid in the upper cell section to flow therein.

In an embodiment, the chamber can be a rotating cylindrical chamber.

In another embodiment, the fourth portion can include a second porous plate and can be configured to support the porous media in the upper cell section and prevent particle migration of the porous media from the upper cell section to the lower cell section.

In an additional embodiment, the second porous plate can have a plurality of pores having sizes ranging from about that of the first porous plate to about 100 µm.

In a supplementary embodiment, the second portion can include a first porous plate and can be configured to prevent particle migration of the porous media from the upper cell section to the second portion.

In a further embodiment, the second portion can further include a flange and can be configured to partially encapsulate the first porous plate.

In an embodiment, the first portion can include a head and can be configured to form a top section of the chamber.

In another embodiment, an air bath cooling system can be connected to the heating oven and can be configured to cool the heating oven.

In an additional embodiment, the porous media can be selected from the group consisting of carbonate core plugs, sandstone core plugs, sand packs, glass beads, sintered glasses, and a combination thereof.

In a supplementary embodiment, the at least one fluid can be selected from the group consisting of water, black oil, volatile oil, gas condensate, wet gas, dry gas, and a combination thereof.

In an embodiment, the motorized piston can include a magnetic stirring system embedded therein and can be configured to homogeneously mix the at least one fluid in the lower cell section.

In a further embodiment, the present subject matter relates to a method of using the above system for analyzing at least one property of a fluid, wherein the method can include obtaining the porous media; placing the porous media inside of the upper cell section; injecting the at least one fluid into the upper cell section via the inlet port; continuously heating the porous media and the at least one fluid in the upper cell section via the heating oven; flowing the at least one fluid from the upper cell section through the fourth portion and into the lower cell section; continuously heating the at least one fluid in the fourth portion and the lower cell section via the heating oven; continuously moving the motorized piston vertically upward towards the fourth portion to pressurize the at least one fluid in the lower cell section thereby allowing the at least one fluid in the lower cell section to flow back through the fourth portion and into the upper cell section; continuously pressurizing and heating the at least one fluid flowing back into in the upper cell section as the porous media absorbs the at least one fluid in the upper cell section via the motorized piston and the heating oven, respectively; and analyzing the at least one property of the at least one fluid in the upper cell section as the porous media absorbs the at least one fluid in the upper cell section.

In an embodiment, the heating steps can include continuously and uniformly heating the porous media in the upper cell section, the at least one fluid in the upper cell section, the at least one fluid flowing through the fourth portion, and the at least one fluid in the lower cell section up to about 200° C.

In another embodiment, prior to the analyzing step, gas bubble formation and/or fog formation can be generated from the at least one fluid as the porous media absorbs the at least one fluid in the upper cell section while the at least one fluid in the upper cell section is being continuously pressurized and heated.

In an additional embodiment, the at least one property of the at least one fluid in the upper cell section can be the gas bubble formation and/or the fog formation.

In a supplementary embodiment, the analyzing step can include observing, via the visualization window, the gas bubble formation and/or the fog formation flowing from the at least one fluid in the upper cell section through the section portion into the visualization window.

These and other features of the present subject matter will become readily apparent upon further review of the following specification.

BRIEF DESCRIPTION OF DRAWINGS

FIG. 1 depicts a system for analyzing at least one property of a fluid.

Similar reference characters denote corresponding features consistently throughout the attached drawings.

DETAILED DESCRIPTION

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a system, and particularly to a system and a method of using the system for analyzing at least one property of a fluid. In certain embodiments, the present subject matter relates to a system and a method of using the system for analyzing at least one property of a fluid, such as a petroleum reservoir fluid, as the fluid is being absorbed by a porous media.

FIG. 1 depicts, in an embodiment, a system (100) for analyzing at least one property of a fluid. The system can include a pressure-volume-temperature (PVT) cell (105). The pressure-volume-temperature (PVT) cell (105) can include a chamber (110) and a heating oven (115), which can completely or partially enclose the chamber (110). The heating oven (115) can be configured to heat the chamber (110). In an embodiment, the pressure-volume-temperature (PVT) cell (105) can be rotated with a primary motor (not shown) attached to the pressure-volume-temperature (PVT) cell (105). Alternatively, in another embodiment, the pressure-volume-temperature (PVT) cell (105) can be integrated with a fluid evaluation unit (120) for providing rotation to the pressure-volume-temperature (PVT) cell (105) via a secondary motor (not shown) attached to the fluid evaluation unit (120). In an embodiment, an air bath cooling system (125) can be connected to the heating oven (115) and can be configured to cool the heating oven (115) thereby cooling the chamber (110). Alternatively, in another embodiment, the heating oven (115) can be cooled by surrounding air thereby cooling the cooling chamber (110).

In another embodiment, the chamber (110) can be a cylindrical chamber. In a non-limiting embodiment, the chamber (110) can have a fluid volume capacity of about 500 cm³. In another non-limiting embodiment, the chamber (110) can withstand pressure up to about 20,000 psi and a temperature range of about ambient temperature (i.e., about 15° C. to about 25° C.) to about 200° C. In a further non-limiting embodiment, the chamber (110) can be made of steel and can be selected from the group consisting of copper steel, nickel steel, chromium steel, titanium steel, aluminum steel, stainless steel, Hastelloy C grade steel, and a combination thereof. The stainless steel can be alloyed with about 10% to about 20% of chromium, nickel, silicon, and manganese. Alternatively, in certain non-limiting embodiments, the chamber (110) can be made of a transparent quartz glass for viewing the inside of the chamber (110). The chamber (110) can include a first portion (130), a second portion (135), a third portion (140), a fourth portion (145), and a fifth portion (150), with the second portion (135), the third portion (140), and the fourth portion (145) located sequentially between the first portion (130) and the fifth portion (150).

In an additional embodiment, the first portion (130) can include a head (155) and can be configured to form a top section of the chamber (110). The second portion (135) can include a flange (160), a first o-ring (165), and a first porous plate (170), with the first o-ring (165) located between the flange (160) and the first porous plate (170). The first porous plate (170) and the first o-ring (165) can be removably fastened to the flange (160) via a plurality of primary screws (175). The flange (160) can be removably attached to the third portion (140) of the chamber (110). The flange (160) can be configured to partially encapsulate the first porous plate (170) and the first o-ring (165).

In one non-limiting embodiment, the first porous plate (170) can be made of metal and can have a thickness of about 1.5 mm. In some non-limiting embodiments, the first porous plate (170) can have a plurality of pores having sizes ranging from about 2 mm to about 100 μm. The first porous plate (170) can be configured to prevent particle migration of a porous media (180) from an upper cell section (185) to the second portion (135) as described herein. It should be understood that the plurality of pores of the first porous plate (170) can have other sizes based on the type of the porous media (180) used in the upper cell section (185) without departing from the present subject matter. The first porous plate (170) can also be configured to allow evolved gases (i.e., gas bubble formation and/or the fog formation) generated from the at least one fluid in the upper cell section (185) to pass therethrough as described herein.

In a supplementary embodiment, a porthole (190) can be formed between the head (155) and the flange (160). A transparent visualization window (195) can be located within the porthole (190). In a non-limiting embodiment, the transparent visualization window (195) can be made of quartz glass. In an embodiment, a first outlet end (200) and a second outlet end (205) of the transparent visualization window (195) can extend through the head (155) and the flange (160), respectively. In this respect, the transparent visualization window (195) can be in communication with the first portion (130) and the second portion (135). An outlet port (210) can be in communication with the first outlet end (200) of the transparent visualization window (195). As another non-limiting embodiment, the outlet port (210) can have an inner dimeter size of about 0.125 inches. The outlet port (210) can be configured to discharge the evolved gases mentioned. A first valve (215) can be located on the outlet port (210) and can be configured to regulate the amount of the evolved gases mentioned passing through the outlet port (210). The second outlet end (205) of the transparent visualization window (195) can be in communication with the first porous plate (170) and can be configured to allow the evolved gases mentioned to pass through the transparent visualization window (195) and into the outlet port (210). In this regard, the evolved gases mentioned passing through the transparent visualization window (195) can be observed via the porthole (190).

In a further embodiment, a light source (220) can be connected to an interior surface of the heating oven (115) and can be located adjacent to an exterior of the porthole (190). The light source (220) can provide light to the transparent visualization window (195) thereby facilitating observance of the evolved gases mentioned passing through the transparent visualization window (195). In an embodiment, the observance of the evolved gases mentioned passing through the transparent visualization window (195) can be done by a user looking through the porthole (190). Alternatively, in another embodiment, the observance of the evolved gases mentioned passing through the transparent visualization window (195) can be done by a digital camera (225). The digital camera (225) can be located adjacent to an exterior of the porthole (190). The digital camera (225) can be attached to an exterior of the heating oven (115), a supporting rail (not shown), or a frame (not shown). The digital camera (225) can be in communication with a computer (not shown) with an integrated liquid/gas interface recognition software. The integrated liquid/gas interface recognition software can display video, via the digital camera (225), of the evolved gas mentioned passing through the transparent visualization window (195) on the computer screen in real-time.

In an embodiment, the third portion (140) can include the upper cell section (185) located therein. The upper cell section (185) can be configured to receive the porous media (180) and at least one fluid injected therein. The porous media (180) and the injected at least one fluid in the upper cell section (185) can be heated by the chamber (110) via the heating oven (115). In another non-limiting embodiment, the porous media (180) can have a fixed length of about 15.24 cm. The porous media (180) can be selected from the group consisting of carbonate core plugs, sandstone core plugs, sand packs, glass beads, sintered glasses, and a combination thereof. The porous media (180) from the group mentioned can be natural or synthetic material. The at least one fluid can be petroleum fluid which can be selected from the group consisting of water (brackish water), black oil, volatile oil, gas condensate, wet gas, dry gas, and a combination thereof. The at least one fluid can be injected into the upper cell section (185) via an inlet port (230).

In a further non-limiting embodiment, the inlet port (230) can have an inner dimeter size of about 0.125 inches. One end of the inlet port (230) can be extended through the third portion (140) of the chamber (110) and into an interior wall (235) of the chamber (110). In this aspect, the one end of the inlet port (230) can be in communication with the upper cell section (185). Another end of the inlet port (230) can be located between the heating oven (115) and the chamber (110). A second valve (240) can be located on the inlet port (230) and can be configured to regulate the amount of the at least one fluid passing through the inlet port (230) and into the upper cell section (185).

In another embodiment, the fourth portion (145) can include a second porous plate (245) and a second o-ring (250). The second porous plate (245) and the second o-ring (250) can be removably fastened to portions of the chamber (110) via a plurality of secondary screws (255). The second porous plate (245) can be configured to support the porous media (180) in the upper cell section (185). In certain non-limiting embodiments, the second porous plate (245) can be made of metal and can have a thickness of about 1.5 mm. The second porous plate (245) can have a plurality of pores having sizes ranging from about 2 mm to about 100 µm. The second porous plate (245) can prevent particle migration of the porous media (180) from the upper cell section (185) to the lower cell section (260) as described herein. It should be understood that the plurality of pores of the second porous plate (245) can have other sizes based on the type of the porous media (180) used in the upper cell section (185) without departing from the present subject matter.

In an additional embodiment, the fifth portion (150) can include the lower cell section (260), a motorized piston (265), a pressure sensor (270), and a temperature sensor (275). The lower cell section (260) can be configured to receive the at least one fluid flowing from the upper cell section (185) through the fourth portion (145), via the second porous plate (245), into the fifth portion (150). The at least one fluid flowing through the second porous plate (245) and into the lower cell section (260) can be heated by the chamber (110) via the heating oven (115). The motorized piston (265) can be configured to vertically move within the fifth portion (150) thereby changing a volume of the lower cell section (260). In this regard, the pressure and the volume of the at least one fluid in the lower cell section (260) can be controlled.

In a supplementary embodiment, the motorized piston (265) can be moved vertically by a displacement device (280). The displacement device (280) can be selected from the group consisting of a volumetric pump, a hydraulic jack system, an electric jack system, a mechanical drive system, and a combination thereof. The displacement device (280) can include a position encoder (not shown) and can be configured to measure the movement and the position of the motorized position (265), therefore the volume of the at least fluid in the lower cell section (260). The motorized piston (265) can include a magnetic stirring system (285) embedded therein and can be configured to homogeneously mix the at least one fluid in the lower cell section (260). The pressure sensor (270) and the temperature sensor (275) can be located within holes (not shown) of the interior wall (235) of the chamber (110). The pressure sensor (270) and the temperature sensor (275) can be configured to measure the pressure and the temperature within the lower cell section (260), respectively. In an embodiment, the position encoder, the pressure sensor (270), and the temperature sensor (275) can be in communication with the integrated liquid/gas interface recognition software via the computer. In this regard, within the lower cell section (260), the volume of the at least one fluid, the pressure, and the temperature can be displayed on the computer screen in real-time.

In a further embodiment, the present subject matter relates to a method of using the above system (100) for analyzing at least one property of a fluid such as, by way of non-limiting example, a petroleum reservoir fluid. The method can include one or more of the following steps, in any combination: obtaining a porous media (180); placing the porous media (180) inside of the upper cell section (185); injecting the at least one fluid into the upper cell section (185) via the inlet port (230); continuously heating the porous media (180) and the at least one fluid in the upper cell section (185) via the heating oven (115); flowing the at least one fluid from the upper cell section (185) through the fourth portion (145) and into the lower cell section (260); continuously heating the at least one fluid in the fourth portion (145) and the lower cell section (260) via the heating oven (155); continuously moving the motorized piston (265) vertically upward towards the fourth portion (145) to pressurize the at least one fluid in the lower cell section (260) thereby allowing the at least one fluid in the lower cell section (260) to flow back through the fourth portion (145) and into the upper cell section (185); continuously pressurizing and heating the at least one fluid flowing back into the upper cell section (185) as the porous media (180) absorbs the at least one fluid in the upper cell section (185) via the motorized piston (265) and the heating oven (115), respectively; and analyzing the at least one property of the at least one fluid in the upper cell section (185) as the porous media (180) absorbs the at least one fluid in the upper cell section (185).

In an embodiment, the method can include continuously rotating the chamber (110) and the heating oven (115) as the at least one fluid is being injected into the upper cell section (185). In this regard, particle(s) from the porous media (180) may migrate away from the porous media (180) during the rotation step. As mentioned previously, the first porous plate (170) and the second porous plate (245) can be configured to prevent the particle(s) migrating from the upper cell section (185) to the second portion (135) and from the upper cell section (185) to the lower cell section (260), respectively.

In another embodiment, the heating steps can include continuously and uniformly heating one or more, or all, of the porous media (180) in the upper cell section (185), the at least one fluid in the upper cell section (185), the at least one fluid flowing through the fourth portion (145), and the at least one fluid in the lower cell section (260) up to about 200° C. In a supplementary embodiment, the vertically upward motion of the motorized piston (265) step can include homogeneously mixing the at least one fluid in the lower cell section (260) via the magnetic stirring system (285) embedded in the motorized piston (265).

In a further embodiment, prior to the analyzing step, gas bubble formation and/or fog formation (evolved gases) from the at least one fluid can be generated as the porous media (180) absorbs the at least one fluid in the upper cell section

9

(185) while the at least one fluid in the upper cell section (185) is being continuously pressurized and heated. In this regard, the generated gas bubble formation and/or fog formation can flow through the first porous plate (170) into the transparent visualization window (195) and into the outlet port (210) to be discharged therefrom. In an embodiment, the at least one property of the at least one fluid in the upper cell section (185) can be the gas bubble formation and/or the fog formation. In this aspect, the analyzing step can include observing, via the visualization window (195), the gas bubble formation and/or the fog formation flowing from the at least one fluid in the upper cell section (185) through the section portion (135) into the visualization window (195).

In an another embodiment, after the analyzing step, the porous media (180) in the upper cell section (185), the at least one fluid in the upper cell section (185), the at least one fluid flowing through the fourth portion (145), and/or the at least one fluid in the lower cell section (260) can be cooled by the heating oven (115) via the air bath cooling system (125) or by the surrounding air. The air bath cooling system (125) can provide cooling to about −20° C.

In an embodiment, the upper cell section (185) can be injected with water, black oil, volatile oil, and a combination thereof as the at least one fluid. In this regard, the pressure-volume-temperature (PVT) cell (105) can be positioned right side up as shown in FIG. 1. Alternatively, in another embodiment, the upper cell section (185) can be injected with gas condensate, wet gas, dry gas, and a combination thereof as the at least one fluid. In this respect, the pressure-volume-temperature (PVT) cell (105) can be inverted.

By integrating the porous media (180) into the PVT cell (105), the porous media (180) can take into account effects of rock properties and rock-fluid interactions on fluid phase behavior, as observed in a typical petroleum reservoir. The rock properties can include porosity, permeability, fracture networks, wettability, capillary pressure, compressibility, pore size distribution, and tortuosity. These factors influence pressure distribution, fluid distribution, fluid saturation, capillary effects, and fluid trapping, thereby affecting fluid properties of the at least one fluid. The fluid properties can include saturation pressure, dew point pressure, volume of gas evolving from oil, volume of liquid dropout from gas condensate, and phase behaviors.

It is to be understood that the system and the method of using the system for analyzing at least one property of a fluid are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A system comprising:
   a rotating cylindrical chamber comprising a first portion, a second portion, a third portion, a fourth portion, and a fifth portion, with the second portion, the third portion, and the fourth portion located sequentially between the first portion and the fifth portion;
   an upper cell section located within the third portion configured to receive a porous media and at least one fluid injected therein, the porous media being selected from the group consisting of carbonate core plugs, sandstone core plugs, sand packs, glass beads, sintered glasses, and a combination thereof;

the second portion including a first porous plate configured to prevent particle migration of the porous media from the upper cell section to the second portion;
   a lower cell section located within the fifth portion configured to receive the at least one fluid flowing from the upper cell section through the fourth portion into the fifth portion;
   a motorized piston located within the fifth portion configured to pressurize the at least one fluid in the lower cell section;
   an inlet port in communication with the upper cell section configured to inject the at least one fluid into the upper cell section;
   a heating oven enclosing the chamber configured to heat the porous media and the at least one fluid in the upper cell section, the fourth portion, and the lower cell section; and
   a visualization window in communication with the first portion and the second portion configured to allow gas bubble formation and/or fog formation generated from the at least one fluid in the upper cell section to flow therein.

2. The system of claim 1, wherein the fourth portion comprises a second porous plate configured to support the porous media in the upper cell section and prevent particle migration of the porous media from the upper cell section to the lower cell section.

3. The system of claim 2, wherein the second porous plate comprises a plurality of pores having sizes ranging from about first porous to about 100 μm.

4. The system of claim 1, wherein the second portion further comprises a flange configured to partially encapsulate the first porous plate.

5. The system of claim 1, wherein the first portion comprises a head configured to form a top section of the chamber.

6. The system of claim 1, further comprising an air bath cooling system connected to the heating oven configured to cool the heating oven.

7. The system of claim 1, wherein the at least one fluid is selected from the group consisting of water, black oil, volatile oil, gas condensate, wet gas, dry gas, and a combination thereof.

8. The system of claim 1, wherein the motorized piston comprises a magnetic stirring system embedded therein configured to homogeneously mix the at least one fluid in the lower cell section.

9. A method of using the system of claim 1 for analyzing at least one property of a fluid, the method comprising:
   obtaining the porous media;
   placing the porous media inside of the upper cell section;
   injecting the at least one fluid into the upper cell section via the inlet port;
   continuously heating the porous media and the at least one fluid in the upper cell section via the heating oven;
   flowing the at least one fluid from the upper cell section through the fourth portion and into the lower cell section;
   continuously heating the at least one fluid in the fourth portion and the lower cell section via the heating oven;
   continuously moving the motorized piston vertically upward towards the fourth portion to pressurize the at least one fluid in the lower cell section thereby allowing the at least one fluid in the lower cell section to flow back through the fourth portion and into the upper cell section;

continuously pressurizing and heating the at least one fluid flowing back into the upper cell section as the porous media absorbs the at least one fluid in the upper cell section via the motorized piston and the heating oven, respectively; and analyzing the at least one property of the at least one fluid in the upper cell section as the porous media absorbs the at least one fluid in the upper cell section.

10. The method of claim 9, wherein the porous media is selected from the group consisting of carbonate core plugs, sandstone core plugs, sand packs, glass beads, sintered glasses, and a combination thereof.

11. The method of claim 9, wherein the at least one fluid is selected from the group consisting of water, black oil, volatile oil, gas condensate, wet gas, dry gas, and a combination thereof.

12. The method of claim 9, wherein the motorized piston comprises a magnetic stirring system embedded therein configured to homogeneously mix the at least one fluid in the lower cell section.

13. The method of claim 9, wherein the fourth portion comprises a second porous plate configured to support the porous media in the upper cell section and prevent particle migration of the porous media from the upper cell section to the lower cell section.

14. The method of claim 9, wherein the heating steps comprise continuously and uniformly heating the porous media in the upper cell section, the at least one fluid in the upper cell section, the at least one fluid flowing through the fourth portion, and the at least one fluid in the lower cell section up to about 200° C.

15. The method of claim 9, prior to the analyzing step, generating gas bubble formation and/or fog formation from the at least one fluid as the porous media absorbs the at least one fluid in the upper cell section while the at least one fluid in the upper cell section is being continuously pressurized and heated.

16. The method of claim 15, wherein the at least one property of the at least one fluid in the upper cell section comprises the gas bubble formation and/or the fog formation.

17. The method of claim 16, wherein the analyzing step comprises observing, via the visualization window, the gas bubble formation and/or the fog formation flowing from the at least one fluid in the upper cell section through the section portion into the visualization window.

* * * * *